(12) United States Patent
Young et al.

(10) Patent No.: US 9,211,228 B2
(45) Date of Patent: Dec. 15, 2015

(54) MASSAGING TOPICAL OILS APPLICATOR

(71) Applicant: Young Living Essential Oils, Lehi, UT (US)

(72) Inventors: D. Gary Young, Alpine, UT (US); Son Q. Le, Orem, UT (US); James T. Davis, II, Springville, UT (US); Marc Schreuder, Provo, UT (US); Cole Woolley, Orem, UT (US)

(73) Assignee: Young Living Essential Oils, LC, Lehi, UT (US)

( * ) Notice: Subject to any disclaimer, the term of this patent is extended or adjusted under 35 U.S.C. 154(b) by 136 days.

(21) Appl. No.: 14/029,541

(22) Filed: Sep. 17, 2013

(65) Prior Publication Data

US 2014/0163443 A1 Jun. 12, 2014

Related U.S. Application Data

(63) Continuation-in-part of application No. 13/458,810, filed on Apr. 27, 2012.

(60) Provisional application No. 61/701,725, filed on Sep. 17, 2012.

(51) Int. Cl.
*A61H 15/00* (2006.01)
*A45D 34/00* (2006.01)
(Continued)

(52) U.S. Cl.
CPC ............ *A61H 15/0085* (2013.01); *A61H 15/02* (2013.01); *A61H 23/0263* (2013.01); *A61H 2015/0064* (2013.01); *A61H 2015/0071* (2013.01); *A61M 35/003* (2013.01)

(58) Field of Classification Search
CPC ..... A45D 34/00; A45D 34/04; A45D 34/041; A61H 15/02; A61H 2201/105; A61H 2015/0071; A61H 2015/0007
USPC .......... 401/209, 219–220; 222/196, 559, 561, 222/199, 200, 409; 137/827–829; 251/331
See application file for complete search history.

(56) References Cited

U.S. PATENT DOCUMENTS 721,821 A 3/1903 Myers
1,292,288 A * 1/1919 Fisher ........................... 401/280
(Continued)

FOREIGN PATENT DOCUMENTS

KR 20120007010 1/2012
KR 1020120007010 1/2012

OTHER PUBLICATIONS

U.S. Appl. No. 13/458,810, Office Action, Nov. 7, 2014.
(Continued)

*Primary Examiner* — Justine Yu
*Assistant Examiner* — Christopher Miller
(74) *Attorney, Agent, or Firm* — Kunzler Law Group, PC (57) ABSTRACT

A massaging applicator device for applying topical oils to an individual, such as a person or creature, and methods of applying topical oils are disclosed. Some embodiments of an exemplary massaging applicator device may include an applicator body containing a vibration assembly. A roller ball foot is coupled to the applicator body. The roller ball foot houses a roller ball. A container is selectively coupled to the roller ball foot and is configured to hold a topical oil. A flow switch is disposed between the container and the roller ball to selectively control flow of topical oil from the container to the roller ball.

18 Claims, 8 Drawing Sheets

(51) Int. Cl.
*A61H 15/02* (2006.01)
*A61H 23/02* (2006.01)
*A61M 35/00* (2006.01)

(56) References Cited

U.S. PATENT DOCUMENTS

| | | | | |
|---|---|---|---|---|
| 2,937,392 | A * | 5/1960 | Williams | 401/213 |
| 4,037,977 | A * | 7/1977 | Ronai | 401/209 |
| 4,270,526 | A * | 6/1981 | Morales et al. | 601/154 |
| 4,326,508 | A * | 4/1982 | Stauffer | 601/129 |
| 4,492,223 | A * | 1/1985 | Burke | 601/154 |
| 4,571,106 | A | 2/1986 | Scuderi | |
| 4,823,777 | A | 4/1989 | Goncalves et al. | |
| 5,131,384 | A * | 7/1992 | Obagi | 601/131 |
| 5,445,596 | A * | 8/1995 | Grace | 601/154 |
| 5,553,957 | A * | 9/1996 | Dornbusch | A45D 34/041 401/209 |
| 5,934,296 | A * | 8/1999 | Clay | 132/320 |
| 6,010,264 | A | 1/2000 | Scuderi et al. | |
| 6,857,806 | B2 * | 2/2005 | Harrison | A45D 34/041 401/208 |
| 6,896,161 | B2 * | 5/2005 | Patz | B65D 47/246 222/484 |
| 6,911,010 | B2 | 6/2005 | Dirks et al. | |
| 6,925,672 | B1 | 8/2005 | Bromley | |
| 7,293,930 | B2 | 11/2007 | Chuang | |
| 7,311,462 | B2 | 12/2007 | Kervoalen | |
| 7,425,102 | B1 * | 9/2008 | Velliquette | 401/186 |
| 7,806,612 | B1 | 10/2010 | Wangler | |
| 8,262,592 | B1 * | 9/2012 | Brooks et al. | 601/17 |
| 8,714,853 | B2 | 5/2014 | Sutcliffe et al. | |
| 2004/0149775 | A1 | 8/2004 | Chen | |
| 2005/0169693 | A1 * | 8/2005 | Serio et al. | 401/219 |
| 2005/0249540 | A1 | 11/2005 | Gueret | |
| 2006/0018704 | A1 | 1/2006 | Baines et al. | |
| 2006/0155225 | A1 * | 7/2006 | Murdock et al. | 601/131 |
| 2006/0222445 | A1 | 10/2006 | Chuang | |
| 2007/0083135 | A1 | 4/2007 | Gueret | |
| 2007/0260159 | A1 | 11/2007 | Cagle et al. | |
| 2008/0107474 | A1 * | 5/2008 | Hsieh | 401/216 |
| 2008/0146977 | A1 * | 6/2008 | Hilditch | 601/72 |
| 2008/0154161 | A1 * | 6/2008 | Abbott | 601/113 |
| 2008/0248138 | A1 | 10/2008 | Greco | |
| 2011/0066121 | A1 | 3/2011 | Hoang et al. | |
| 2011/0091265 | A1 * | 4/2011 | Zhang | A45D 34/04 401/195 |
| 2013/0101340 | A1 * | 4/2013 | Liu | 401/208 |

OTHER PUBLICATIONS

Doterra Aromatics, "Orange Wild (*Citrus sinensis*) Oil" and "Frankincense (*Boswellia frereana*) Oil", 2008-2009.
Application No. PCT/US2012/035624, International Preliminary Report on Patentability, Nov. 6, 2014.
PCT/US2012/035624, International Search Report, Jan. 24, 2013.
U.S. Appl. No. 13/458,810, Final Office Action, May 7, 2015.
Doterra Wild Orange Oil and Frankincense Oil, pp. 10, 2008-2009.

* cited by examiner

MASSAGING TOPICAL OILS APPLICATOR

RELATED APPLICATIONS

This application is a continuation in part of U.S. patent application Ser. No. 13/458,810 filed on Apr. 27, 2012, and claims priority to U.S. Provisional Patent Application No. 61/701,725 filed on Sep. 17, 2012, each of which are incorporated by reference in their entirety.

FIELD

This application relates generally to massagers. In particular, this application relates to a massager with one or more roller ball applicators for applying topical oils to an individual, such as a person or a creature.

BACKGROUND

In recent years, sales for essential oils and other topically applied oils have exploded. Topically applied oils are usually oils which are derived from, or include certain essential components or essences of different substances. Such topically applied oils are generally referred to as essential oils.

Essential oils, known as nature's living energy, are the natural, aromatic volatile liquids found in shrubs, flowers, trees, resins, fruit peels, rhizomes, roots, bushes, and seeds. The distinctive components in essential oils defend plants against insects, environmental conditions, and disease. They are also vital for a plant to grow, live, evolve, and adapt to its surroundings. Essential oils are extracted from aromatic plant sources via steam distillation, cold pressing, and other types of distillation. Essential oils are highly concentrated and far more potent than dry herbs. Other topically applied oils and fatty oils may include olive oil, almond oil, coconut oil, etc., and oils high in esters, such as jojoba oil, and waxes such as beeswax.

While essential oils often have a pleasant aroma, their phytochemical makeup is complex and their benefits vast—which make them much more than something that simply smells good. Historically, essential oils have played a prominent role in everyday life. With more than 200 references to aromatics, incense, and ointments throughout the Bible, essential oils are said to be used for anointing and healing the sick. Today, essential oils are used for aromatherapy, massage therapy, emotional health, personal care, nutritional supplements, household solutions, and much more.

Roller ball applicators have been used in many applications. However, roller ball applicators generally use a fairly pliable plastic housing to accommodate the ball in a press-fit assembly. Traditional roller ball assemblies are unsuitable for use with most topical oils, such as essential oils, particularly citrus essential oils (i.e., lemon, orange, grapefruit, bitter orange, yuzu, lime, bergamot, etc.), frankincense, high terpene oils, and other similar oils that can have a potent solvent effect, because the oils tend to impregnate plastics and relax the elasticity or swell the plastic, which often causes the roller ball to become excessively loose and potentially dislodge, or swell the roller ball and generally make plastic containers unsuitable. Additionally, essential oils tend to work as solvents with many plastics and can leach unwanted chemicals, pigments, residual monomers, and compounds from the plastics into the essential oils. Because of this, applicators for topical oils use different application methods and devices that do not require plastics that retain their material properties, and when using essential oils, generally avoid plastics altogether.

SUMMARY

Exemplary massaging applicator devices for applying topical oils to an individual, such as a person or creature, and methods of applying topical oils are disclosed. Some embodiments of an exemplary massaging applicator device may include a body; a vibration assembly disposed within the body; at least one container configured to hold topical oil; and at least one roller ball foot coupled to the body, wherein the container is in fluid communication with the at least one roller ball foot such that the at least one roller ball foot is configured to apply the topical oil. The topical oil may comprise an essential oil.

In some embodiments, the at least one roller ball foot may include a retaining ring formed from metal, such as aluminum. Similarly, the at least one roller ball foot may also include at least two or three, or more roller ball feet. The vibration assembly may be configured to massage an individual contacting the at least one roller ball foot. The fluid communication between the container and the roller ball foot may be selectively closeable. The roller ball is formed from metal or glass and may include surface features.

In some embodiments, topical oil may be applied to an individual by, placing topical oil in at least one container; coupling the at least one container to at least one roller ball foot having a roller ball; placing the roller ball of the at least one roller ball foot against the skin of an individual; applying massaging vibrations through the roller ball to the individual; and moving the at least one roller ball foot such that the roller ball rotates within the at least one roller ball foot and delivers oil to the skin of the individual. The topical oil in various containers may be an essential oil, such as a lavender, citrus, or frankincense, and may be different from the essential oil in another of the containers. In some embodiments, the at least one roller ball foot may include a roller ball housing, and wherein the roller ball is held in the roller ball housing with the retention cap.

In some embodiments, a device for applying topical oils to an individual includes an applicator body, a roller ball foot, a container, and a flow switch. The applicator body contains a vibration assembly. The roller ball foot is coupled to the applicator body and houses a roller ball. The container is selectively coupled to the roller ball foot. The container is configured to hold topical oil. The flow switch is disposed between the container and the roller ball. The flow switch is configured to selectively control flow of topical oil from the container to the roller ball.

In some embodiments, a device for applying topical oils to an individual includes an applicator body, a roller ball foot, a container, and a post. The applicator body contains a vibration assembly. The roller ball foot is coupled to the applicator body. The roller ball foot houses a roller ball. The container is selectively coupled to the roller ball foot. The container is configured to hold topical oil. A channel is formed between the container and the roller ball. The post is disposed with the channel. The post is configured to vibrate within the channel when the vibrational assembly is activated. Vibration of the post may encourage flow of oil through the channel.

In some embodiments, a method of controlling the flow of topical oil in a massaging applicator includes: placing topical oil in at least one container; coupling the at least one container to at least one roller ball foot having a roller ball; applying massaging vibrations to the roller ball; and selectively controlling the flow of a topical oil to the roller ball through a flow switch.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION

This specification describes exemplary embodiments and applications of the invention. The invention, however, is not limited to these exemplary embodiments and applications or to the manner in which the exemplary embodiments and applications operate or are described herein. Moreover, the singular forms "a," "an," and "the" include plural referents unless the context clearly dictates otherwise. Thus, for example, reference to a roller ball includes reference to one or more roller balls. In addition, where reference is made to a list of elements (e.g., elements a, b, and c), such reference is intended to include any one of the listed elements by itself, any combination thereof.

Numerical data may be expressed or presented herein in a range format. It is to be understood that such a range format is used merely for convenience and brevity and thus should be interpreted flexibly to include not only the numerical values explicitly recited as the limits of the range, but also as including all the individual numerical values or sub-ranges encompassed within that range as if each numerical value and sub-range is explicitly recited. As an illustration, a numerical range of "about 1 to 5" should be interpreted to include not only the explicitly recited values of about 1 to 5, but also include individual values and sub-ranges within the indicated range. Thus, included in this numerical range are individual values such as 2, 3, and 4 and sub-ranges such as 1-3, 2-4, and 3-5, etc. This same principle applies to ranges reciting only one numerical value and should apply regardless of the breadth of the range or the characteristics being described.

By the term "substantially" is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

This application relates generally to massagers. In particular, this application relates to a massager with one or more roller ball applicators for applying topical oils to an individual, such as a person or a creature.

Figure 1:
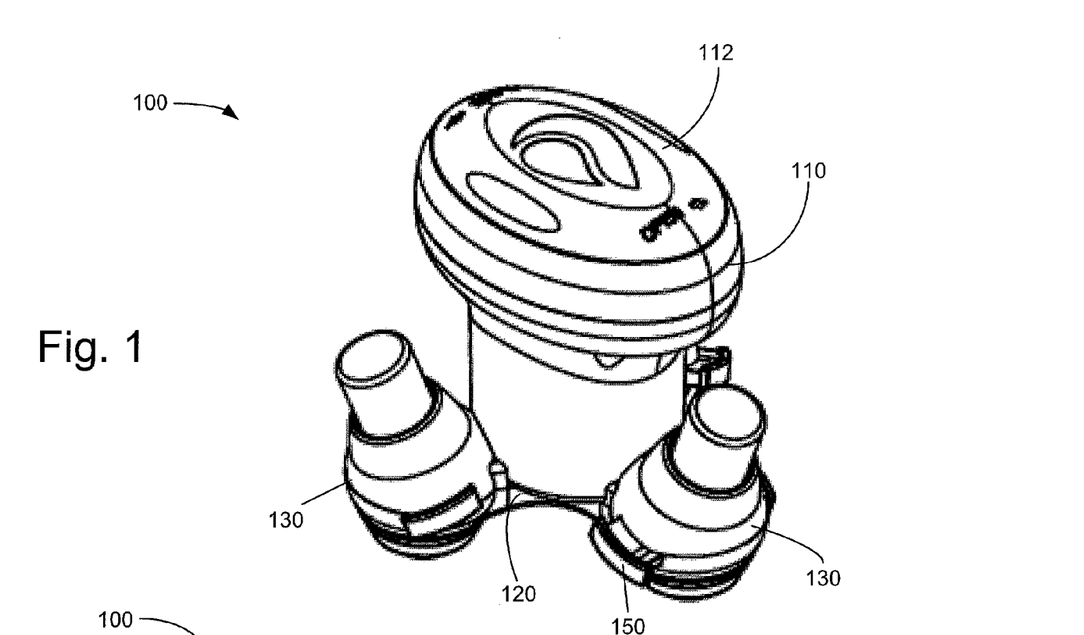
FIG. 1 is a top perspective view of a massaging roller ball topical oil applicator, in accordance with some embodiments of the invention.
Figure 2:
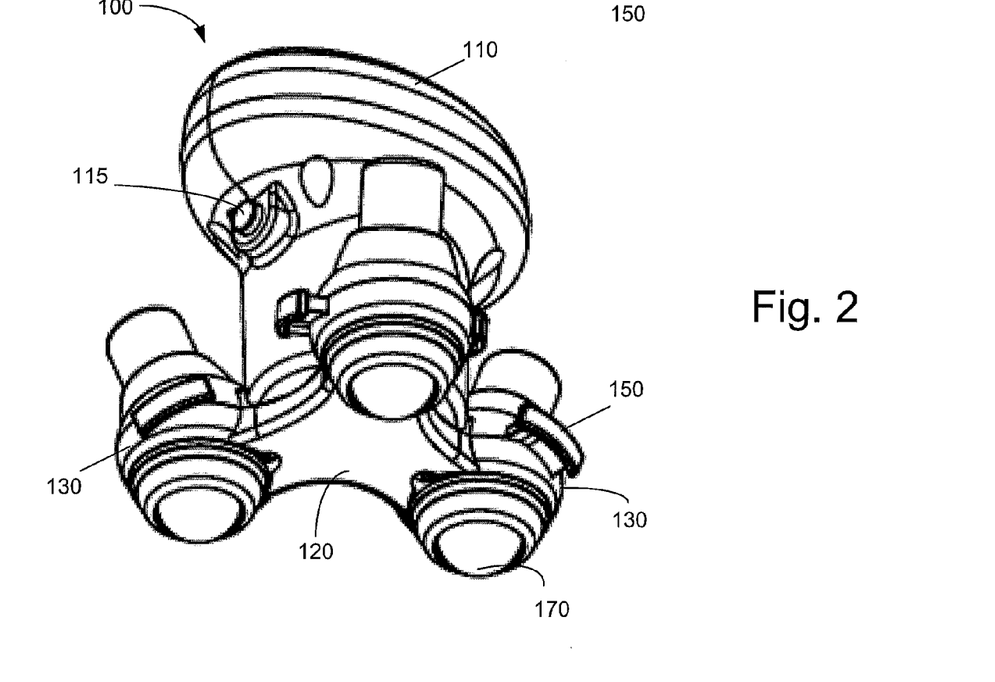
FIG. 2 is a bottom perspective view of the massaging roller ball topical oil applicator of FIG. 1, in accordance with some embodiments of the invention.
Figure 3:
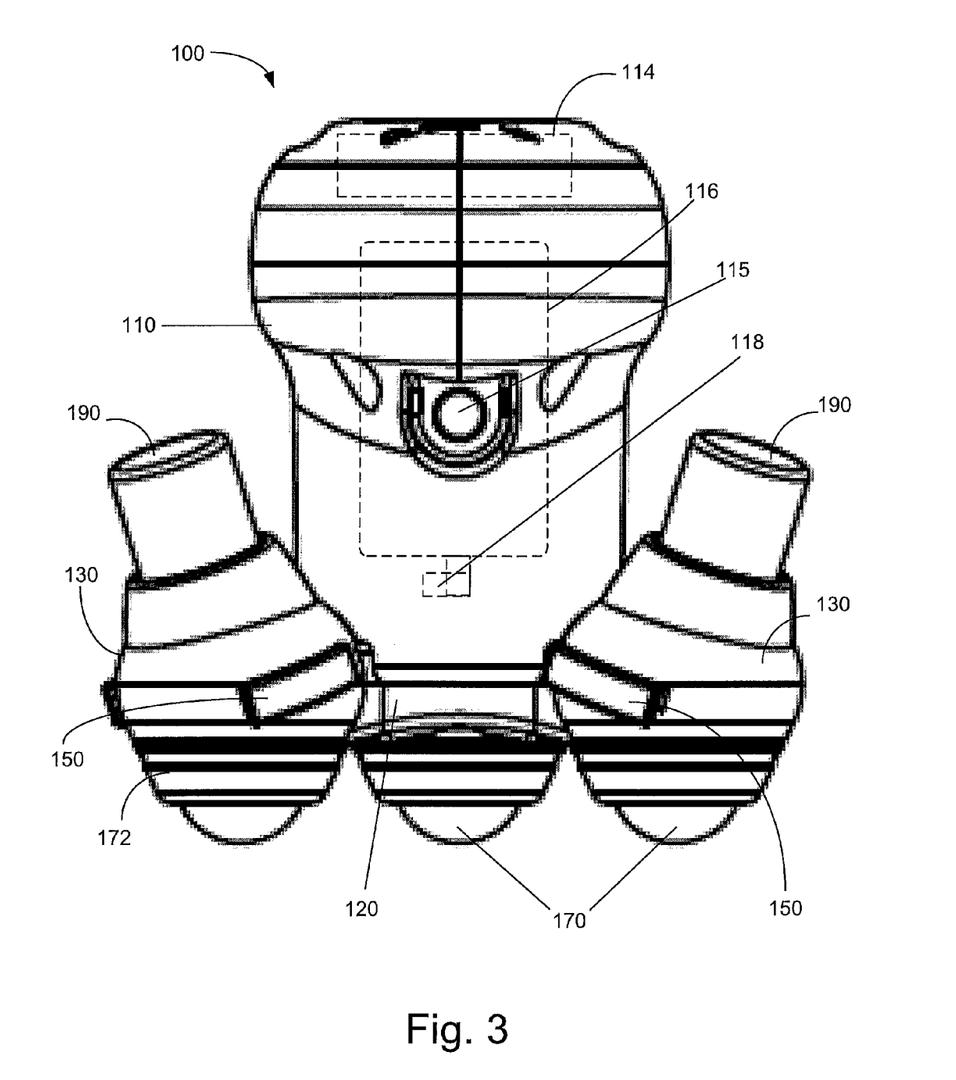
FIG. 3 is a side view of the massaging multiple roller ball topical oil applicator of FIG. 1, in accordance with some embodiments of the invention.

FIGS. 1-3 illustrate a roller ball topical oil applicator 100 (or simply "applicator"), which may be used for massaging and for applying topical oils, such as essential oils to the skin of an individual or other creature. Applicator 100 may include applicator body 110, base 120, and roller ball feet 130, along with oil containers 190. As is shown in the figures, applicator 100 may include three roller ball feet 130. In other embodiments, applicator 100 may include one or more roller ball foot 130. Each roller ball foot 130 may include flow switch 150 and roller ball 170, each of which will be described in further detail below.

Applicator body 110 may include top cover 112 and switch 115. Applicator body 110 may be formed in an ergonomic shape to conform with and be comfortable for a human hand to grasp and use. Applicator body 110 may be formed of any suitable material, such as metal, plastic, wood, or any combination of or composite material. For example, applicator body 110 may be formed of plastic and covered (at least partially) by a vibration dampening and pliable sleeve (not shown), such as of neoprene. Applicator body 110 may be formed a sufficient size and configuration to accommodate a vibration assembly and to allow for bottles 190 to be selectively removed from roller ball feet 130.

As shown in FIG. 3, within applicator body 110 may be located a vibration assembly with batteries 114, motor 116 and eccentric mass 118. Top cover 112 of applicator body 110 may be a battery compartment access door such that top cover 112 may be removed to replace batteries 114. Eccentric mass 118 may rotate when motor 116 is turned on with switch 115, causing vibrations due to the unbalanced rotation of eccentric mass 118. In some embodiments, a control board may be used to control different speeds or functions of the vibration assembly. Similarly, the vibration assembly may be powered with a cord instead of batteries 114, or may include a power management circuit that may be used to charge batteries 114. Similarly, in any embodiment of applicator 100, any suitable massaging or vibration mechanism may be used to provide applicator 100 with a massaging action.

Base 120 may be coupled to applicator body 110 and to roller ball feet 130. Base 120 may be coupled to applicator body 110 with fasteners, such as screws, or may be permanently coupled to applicator body 110 with sonic welding, adhesives, etc. Base 120 may be formed of any suitable material to withstand the forces of having a person push down on applicator body 110 to apply roller ball feet to give a massage to an individual person or creature. Similarly, base 120 may be formed of an oil-resistant material to resist degradation by oils used with applicator 100. For example, base 120 may be formed of certain plastics, metal, ceramic, composites, wood, or any combination of these and other suitable materials.

As shown in FIGS. 1 to 7, the applicator 100 is shown having three roller ball feet 130. As discussed, each of the roller ball feet 130 may have a bottle 190 with oils to be used with applicator 100 is providing a massage. Because there are multiple positions for bottles, different combinations of oils or other fluids may be used with applicator 100. For example, some oil other than an essential oil, such as a mineral oil, baby oil, nut or fruit oil, or vegetable oil may be in one of the bottles 190, while eucalyptus essential oils are in the remaining two bottles 190. Similarly, one or more of the bottles may be empty or not positioned initially such that only one or none of the roller ball feet 130 is able to dispense oil at any given time.

Each roller ball foot 130 may include a flow switch 150 that may be selectively open or closed to selectively control flow of oil from bottle 190 to the roller ball 130 and subsequently to a recipient surface, such as during a massage. By opening or closing one or more flow switches oil from only the desired bottles 190 may be applied during a massage. For example, a specific treatment pattern using different essential oils may be easily affected by keeping two flow switches closed and opening the flow switch 150 of a first desired oil. When enough of the first desired oil is dispensed, or the first oil is depleted, the flow switch 150 of the first desired oil may be closed, and the flow switch 150 of a second desired oil may be opened, and so on. In some embodiments, different combinations of oils may be used to achieve a particular therapy or outcome simultaneously, depending on the order and combinations the oils are used.

Figure 5:
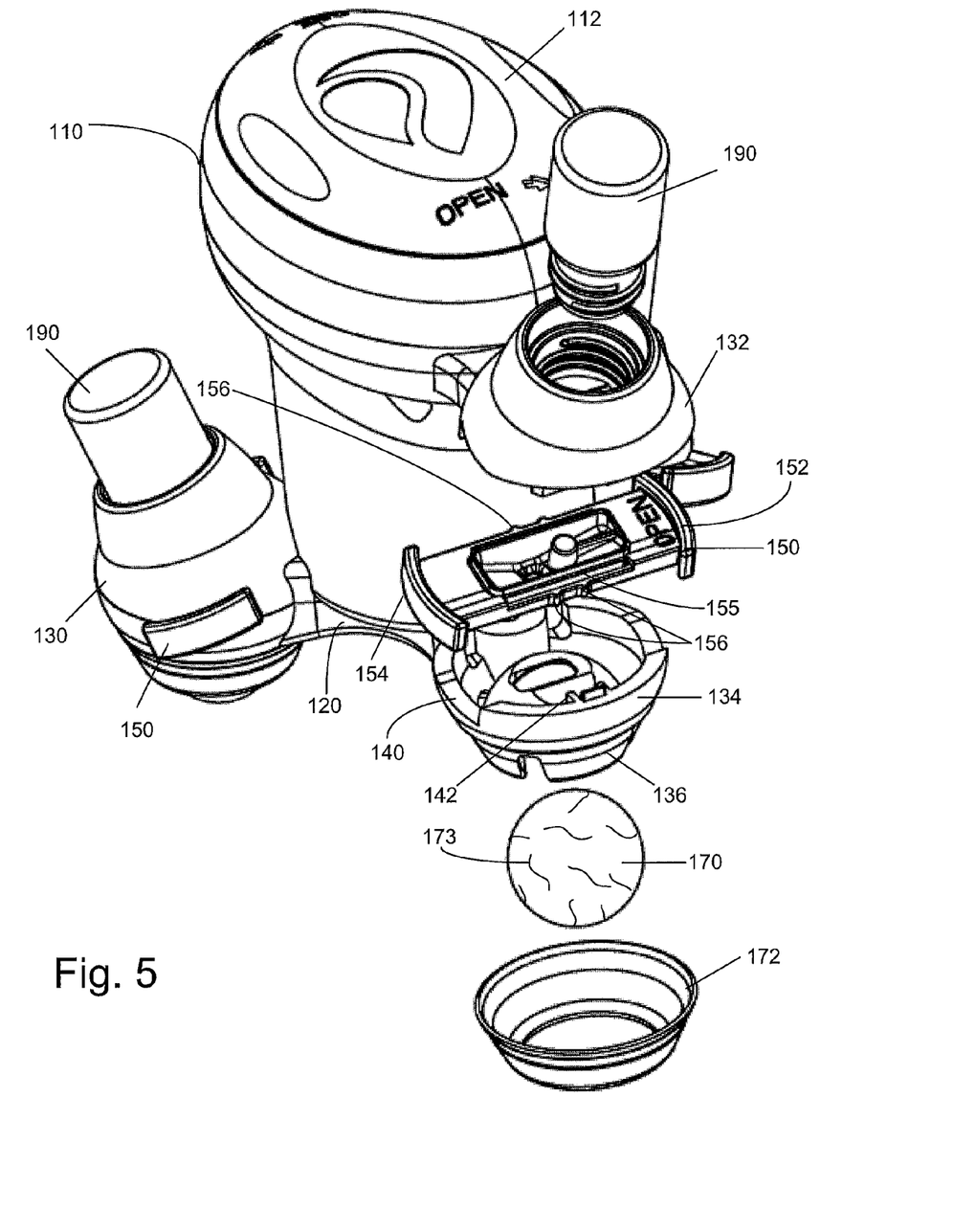
FIG. 5 is a partial exploded view of a massaging multiple roller ball topical oil applicator with a fully exploded roller ball foot, in accordance with some embodiments of the invention.

As shown in FIG. 5, in some embodiments, roller ball 170 may include surface features 173 that may facilitate collecting oils onto roller ball 170 when being used, and may also provide additional tactile stimulation when used during a massage. In some embodiments, surface features 173 may be various patterns or designs, such as with a company logo, geometric pattern, or other desired aesthetic feature that also serves to carry oil. Surface features 173 may be formed in or on the surface of roller ball 170 through any method, such as etching, cutting, grinding, micro-welding, casting, stamping, etc. In some embodiments, a single bottle may be in fluid communication with and be used to supply oil to more than one roller ball foot 130, such as through a tube.

Figure 4:
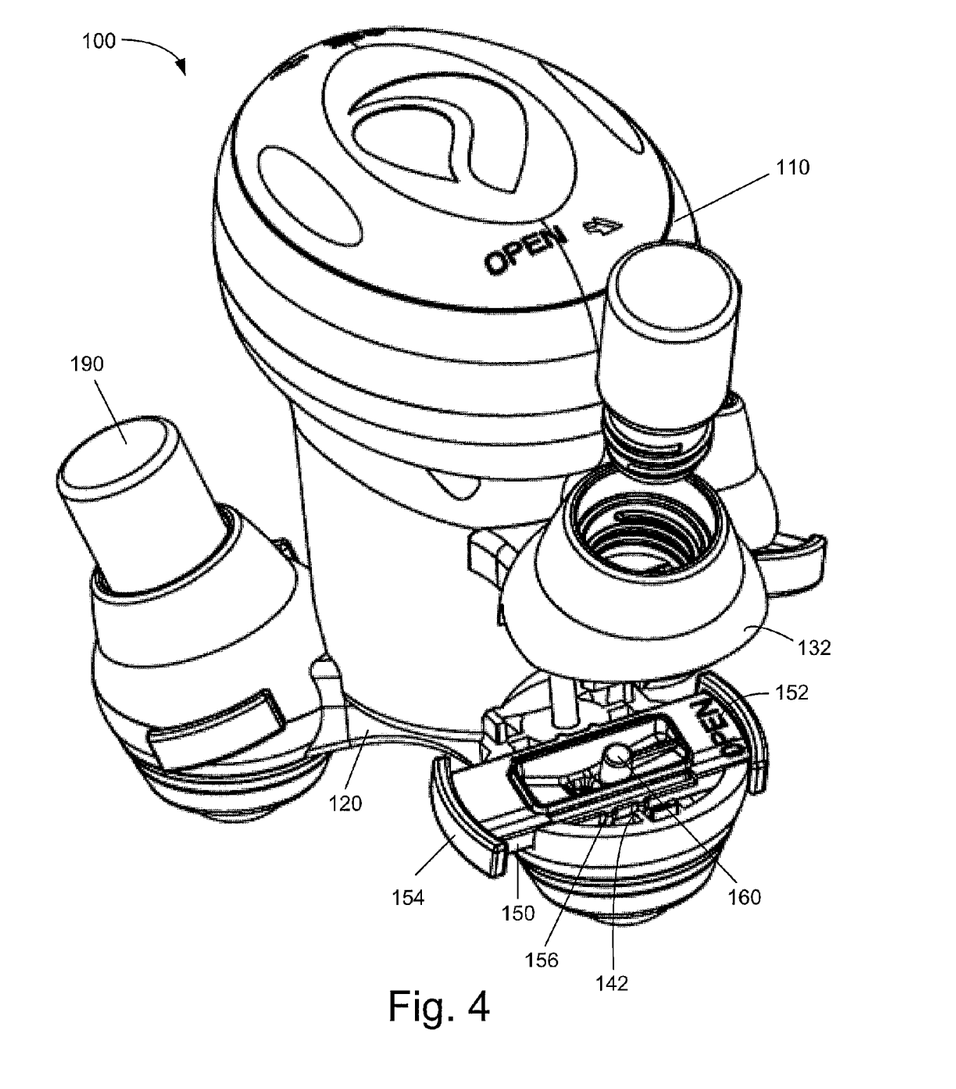
FIG. 4 is a partial exploded view of a massaging multiple roller ball topical oil applicator with a partially exploded roller ball foot, in accordance with some embodiments of the invention.

FIGS. 4-5 illustrate exploded views of roller ball foot 130. Roller ball foot 130 may be formed of any suitable material for use with a massaging essential oil applicator. For example, roller ball foot 130, along with any other component of applicator 100 that may be in contact with essential oils dispensed from applicator 100, may be formed from an oil resistant plastic or other suitable material such as chemically resistant polypropylene, ultem, other homopolymers, etc., or other suitable materials, including materials with oil resistant coatings. Roller ball foot 130 may include top 132, roller ball housing 134, and ball socket 136, configured to accommodate roller ball 170 and retaining ring 172. In some embodiments, roller ball housing 134 may be formed as a portion of base 120, while in other embodiments, roller ball housing 134 may be coupled to base 120 using any suitable fastener, adhesive, coupling or joining method.

Figure 6:
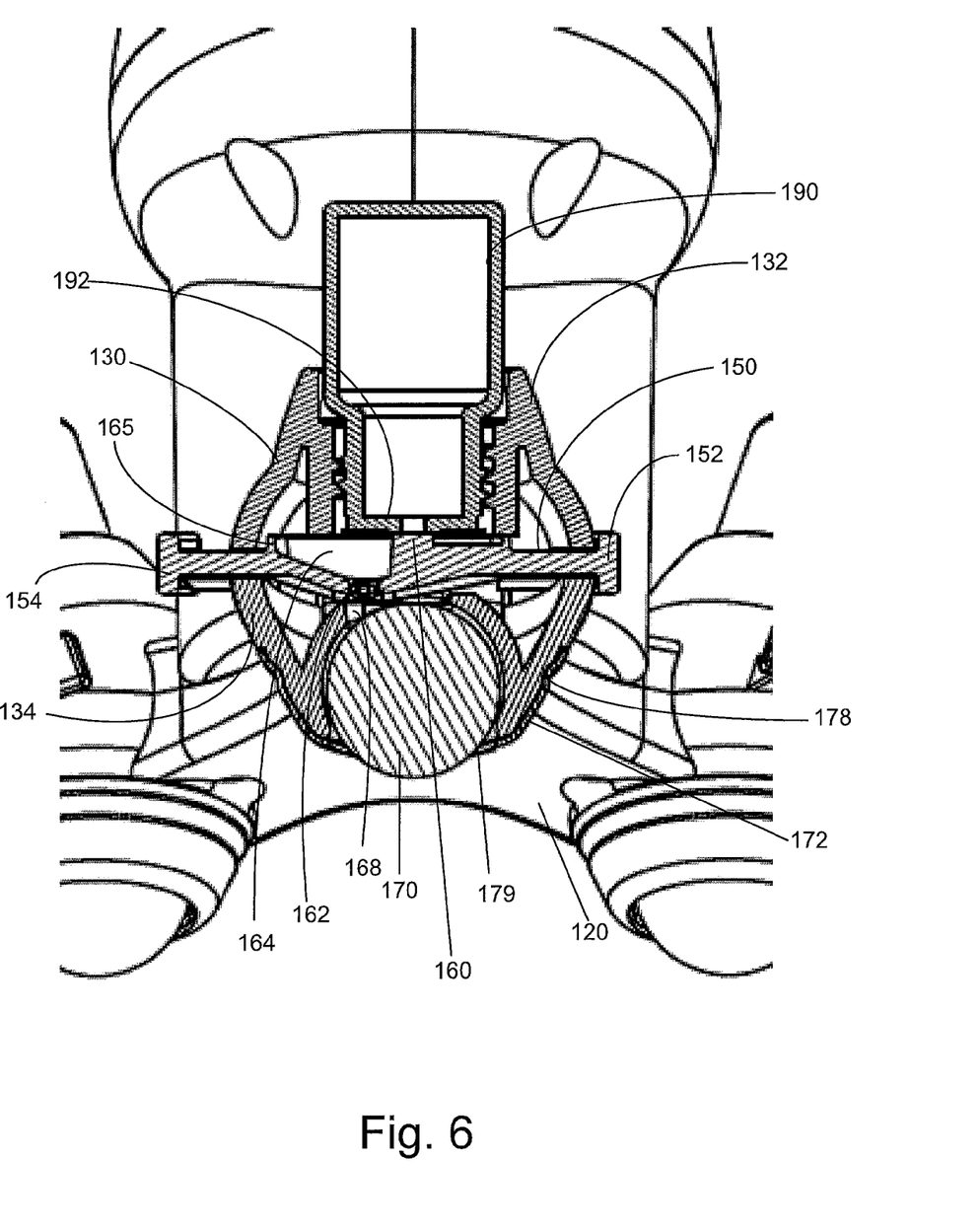
FIG. 6 is cross-sectional views of a roller ball foot of a massaging multiple roller ball topical oil applicator having a flow switch in a closed position, in accordance with some embodiments of the invention.

As best shown in FIG. 6, roller ball housing 134 may also include a groove 178 for holding and working in conjunction with retaining ring 172 to hold roller ball 170 in place in order to apply topical oil. Retaining ring 172 may include ball retainer lip 179, defining a hole in retaining ring 172 through which a portion of roller ball 170 may extend. Retainer lip 179 may have an annular diameter dimension smaller than the diameter of roller ball 170 to secure roller ball 170 in place without allowing roller ball 170 to pass through retaining ring 172 when attached to roller ball housing 134. Retaining ring 172 may also include an indent to cooperate with grove 178 of roller ball housing 134 to hold retaining ring 172 in place on roller ball foot 130, thereby holding roller ball 170 in place. In some embodiments, roller ball 170 may be held in place with a portion of roller ball housing 134 with retaining ring 172 securing roller ball 170 in roller ball foot 130, such that the materials of roller ball foot 130 may not relax beyond the dimensions of retaining ring 172.

Retaining ring 172 may be formed of any suitable material to resist relaxation of roller ball housing 134 if essential oils penetrate the material of roller ball housing 134, thereby keeping roller ball 170 in place. Such materials may include metals, such as aluminum, steel, copper, brass, titanium, or any suitable alloy from these or other metals. Such materials may also include ceramics, carbon fiber, or any other suitable material. In some embodiments retaining ring 172 may be coated or treated to resist corrosion, including, for example, anodizing, Teflon coating, enamel, etc.

Roller ball 170 may be placed in roller ball housing 134 and then retaining ring 172 may be placed onto roller ball housing 134. By pressing retaining ring 172 over the lower portion of roller ball housing 134, indent 178 of retaining ring 172 may snap into place in the groove at an appropriate depth to hold roller ball 170 in place, while also providing appropriate spacing to allow a desired flow of essential oils to be applied with applicator 100. As such, at least one of roller ball housing 134 and retaining ring 172 may be formed of a material that allows for elastic deformation to permit retaining ring 172 to be fitted over roller ball housing 134 as described and illustrated. Roller ball 170 may be formed in any suitable size for use as a massaging implement. Similarly, roller ball 170 may be sized relative to roller ball housing 134 to control the flow rate of oil. For example, a tighter fitting roller ball 170 would allow a slower flow rate than a looser fitting roller ball 170.

Essential oils such as citrus oils, frankincense, oils high in monoterpenes or blends of such oils mixed with other solvents, tend to affect plastics in an aggressive manner. Retaining ring 172 fitted over roller ball housing 134 may allow roller ball housing 134 to be formed of a plastic material that is suitable for use in an aggressive oils environment without losing roller ball 170. Similarly, roller ball 170 may be formed of any suitable material sufficient to maintain a desired fit and alignment with roller ball foot 130 to provide a desired flow-rate of oil at each application. For example, roller ball 170 may be formed of steel, aluminum, ceramic, or any other suitable material.

Slot 140 may be formed in roller ball foot 130 to accommodate flow switch 150. Notches 142 may be provided in roller ball foot 130 to work with protrusions 156 of flow switch 150 to achieve a detent action to hold flow switch 150 in a desired open or closed position. Top 132 and roller ball housing 134 may be coupled together to form slot 140 and hold fluid switch 150 in place by sonic welding, fasteners, glue, or any other suitable component coupling method.

Figure 7:
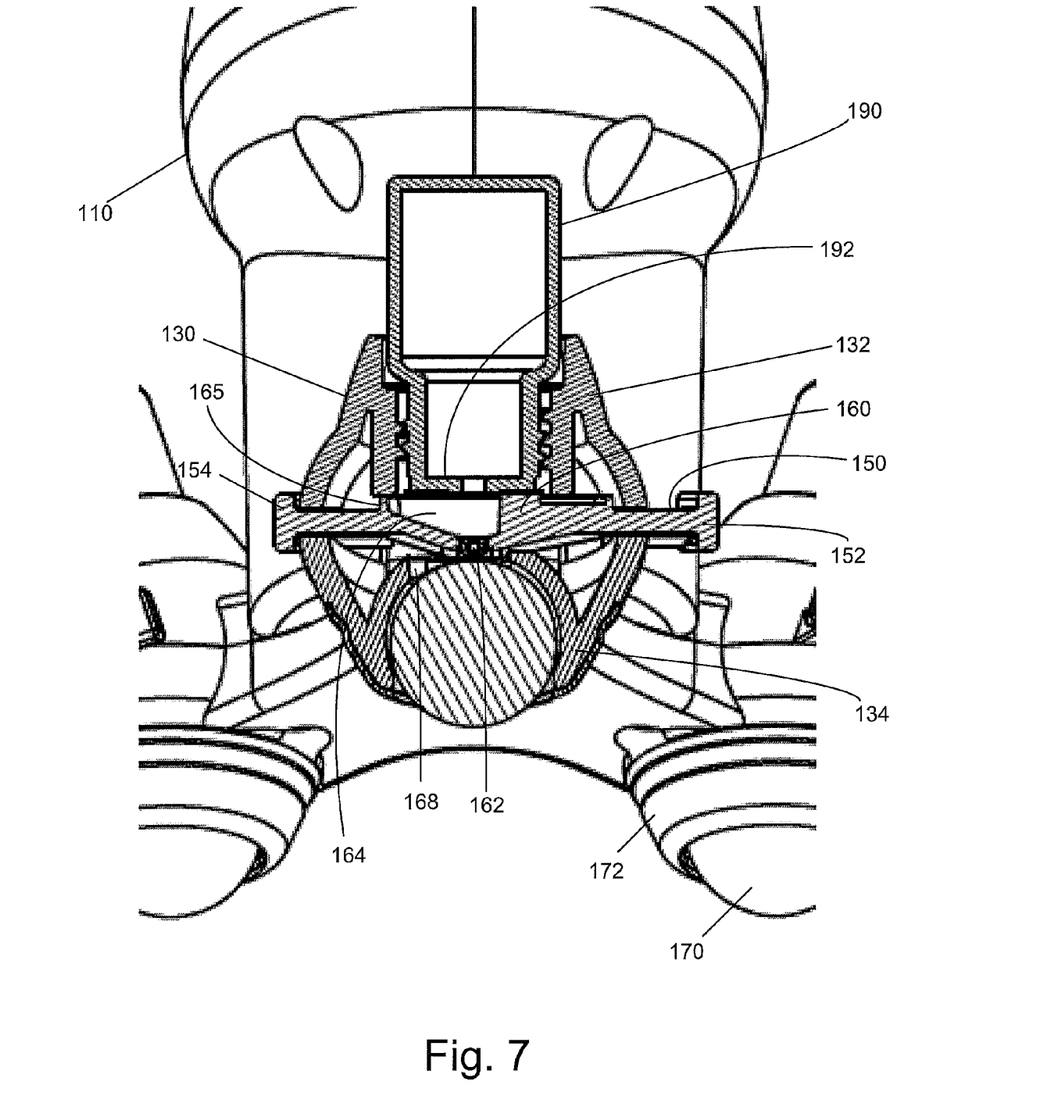
FIG. 7 is cross-sectional views of a roller ball foot of a massaging multiple roller ball topical oil applicator having a flow switch in an open position, in accordance with some embodiments of the invention.

As shown in FIGS. 4 to 8, flow switch 150 may include first end 152 and second end 154. Stopper 160 and well 164 may also be formed in flow switch 150. Stopper 160 may form a sealing surface between flow switch 150 and bottle 190 or flow insert 192 of bottle 190 to prevent oil flow out the bottle when flow switch 150 is in a closed position. Channel 162 may be formed in well 164 of flow switch 150. As mentioned above, protrusions 156 may be formed on the sides of flow switch 150 to provide a detent mechanism to hold flow switch in one of an open position, as shown in FIG. 7, or a closed position, as shown in FIG. 6. Slot 155 may be formed in flow switch 150 to provide resilience for protrusions 156 to push past notches 142 of roller ball foot 130.

As shown in FIGS. 6 and 7, flow switch 150 may be moved between an open position and a closed position. In the open position, well 164 may be positioned below an opening 194 in flow insert 192 of bottle 190, allowing fluid to flow from bottle 190 into well 164 and/or through channel 162, and onto roller ball 170 to be dispensed from roller ball 170 onto any surface against which roller ball 170 is rolled, such as human skin. In the open position, first end 152 extends from roller ball foot 130, revealing an "open" indicia or alternatively a green colored fired end 152, indicating that oil may pass from bottle 190 to roller ball 170 to be dispensed. In the open position, stopper 160 may be positioned away from the opening in bottle insert 192, and seal 165 may be positioned against a portion of top 132 to prevent oil from spilling out of well 164 and into top 132.

As shown in FIG. 6, the flow switch may be selectively moved to the closed position to stop the flow of oil to the roller ball 170. When flow switch 150 is positioned in a closed position, stopper 160 may be positioned over the opening in flow insert 192 of bottle 190. As such, oil may be prevented from exiting bottle 190. In the closed positioned, well 164 may be positioned such that any oil remaining in well 164 may flow through channel 162 and passage 168 to be dispensed by roller ball 170. In either case, applicator 100 may be used in any orientation as a massager, with the orientation being used at times to help regulate the flow rate of oils, as desired.

In order to attach bottles 190 to applicator 100, applicator may be positioned upside down to keep the bottles 190 upright. The bottles 190 may be screwed into receiving positions in each of the top 132 portions of the roller ball feet 130. As shown in the figures, the bottles may be oriented at a slight angle from vertical to accommodate the proximity of roller ball feet 130 and an ease of attaching bottles 190. After each of the bottles (or as many bottles as desired) are seated in top 132 portions, the applicator may be used to massage and dispense oils as desired.

In some embodiments, flow insert 192 may be formed such that even when bottle 190 is held upside down, there is very low, if any flow. In such embodiments, applicator 100 would not need to be inverted to place or exchange bottles 190. In such embodiments, the flow of fluid from bottle 190 would correspond to when the vibration assembly is vibrating, the vibrations facilitating the flow through flow insert 192. As such, in some embodiments, turning on and off switch 115 may control flow of fluids from any of bottles 190. Similarly, the opening in flow insert 192 may be sized to achieve a desired flow rate when in use. For example, a larger opening may provide a faster flow rate and a smaller opening, a lower flow rate.

Bottles 190 may be any container suitable to hold essential oils. Bottles 190 may be formed of glass, metal, plastic, or any other suitable material. Bottles 190 may be removably coupled to roller ball feet 130 using threads as shown in the figures, or with a clamping mechanism, camming locks, or any other method of attaching a fluid container to an applicator.

Figure 8:
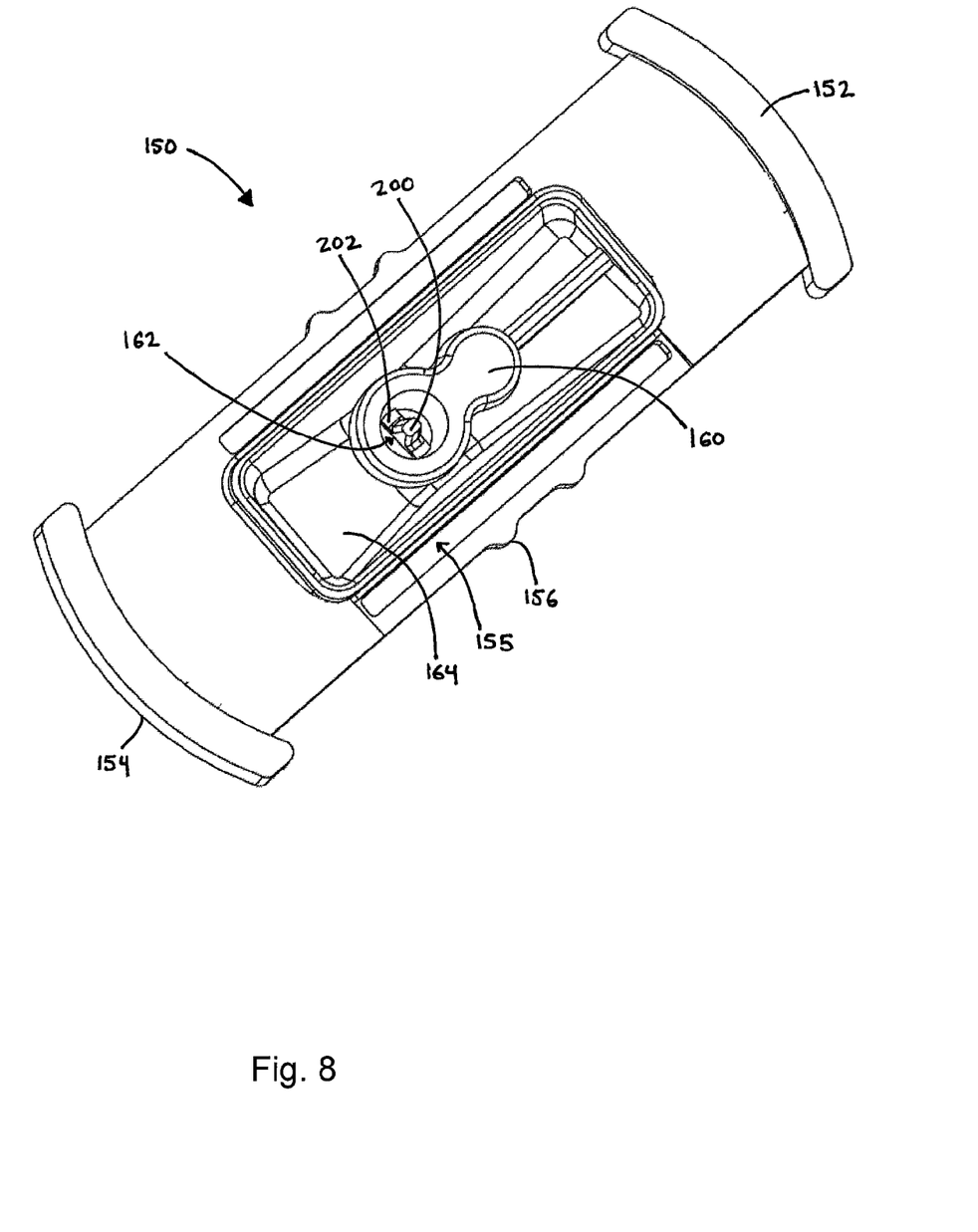
FIG. 8 is an embodiment of an isolated flow switch, in accordance with some embodiments of the invention.

FIG. 8 depicts an embodiment of flow switch 150 having post 200 according to some embodiments. As shown, flow switch 150 can include stopper 160 and channel 162 formed through an extension of stopper 160 (rather than through well 164 as shown in FIGS. 4 to 7). Channel 162 is provided to permit oil to flow through flow switch 150 to roller ball 170 during a massage or when otherwise desired. In some embodiments, channel 162 may be configured to completely or partially limit the flow of fluid through channel 162 to times when applicator 100 is turned on and is vibrating. For example, the shape and size of channel 162 can be configured to prevent fluid flow through channel 162, due to surface tension and/or other physical factors, absent vibration of the application. Such vibration may reduce surface tension and/or other physical forces retaining oil within channel 162 and permit fluid flow.

Additionally, in certain embodiments, as shown in FIG. 8, post 200 may be disposed vertically or semi-vertically (substantially parallel to the inner axis of channel 162) within the interior of channel 162. Post 200 may be connected to the inner surface of channel 162 at only one location along its vertical length, as shown. For example, in the illustrated embodiment, post 200 is connected to the inner surface of channel 162 at only a first end of post 200 (a bottom end when applicator 100 is oriented "upright, as shown in FIG. 1) by post support 202. Alternatively, post 200 may be connected to the inner surface of channel 162 at two or more locations on a single end of its vertical length. Post 200 may also be connected to another portion of flow switch 150 outside of channel 162. When connected to the inner surface of channel 162 at one or more fixed locations(s) along its vertical axis, the non-connected end of post 200 may sway and vibrate in relation to the inner surface of channel 162 when the applicator is operating and vibrating.

When vibrating, post 200 may contact oil that enters channel 162. The vibration of post may affect the oil in such a way as to permit it to flow through and out channel 162. For instance, the vibration may change the physical properties of the oil to permit it to overcome surface tension between the oil and the inner surface of channel 162 to permit it to flow out channel 162. When the post stops vibrating, such as when applicator 100 is turned off, this phenomenon can completely or partially stop, preventing oil from exiting the channel. Thus, in some embodiments, post 200 within channel 162 may provide complete or partial flow control through channel 162, even when flow switch 150 is in the open position.

Post support 202 may have various configurations. As shown in FIG. 8, post support 202 can connect to the inner surface of channel 162 at two locations. In other instances, post support 202 can connect to the inner surface of channel 162 at one location, three locations, or more than three locations. Similarly, while post 200 is shown as having a partially rectangular cross-section, in other embodiments it may have other shaped cross sections, including circular, triangular, etc.

Figure 9:
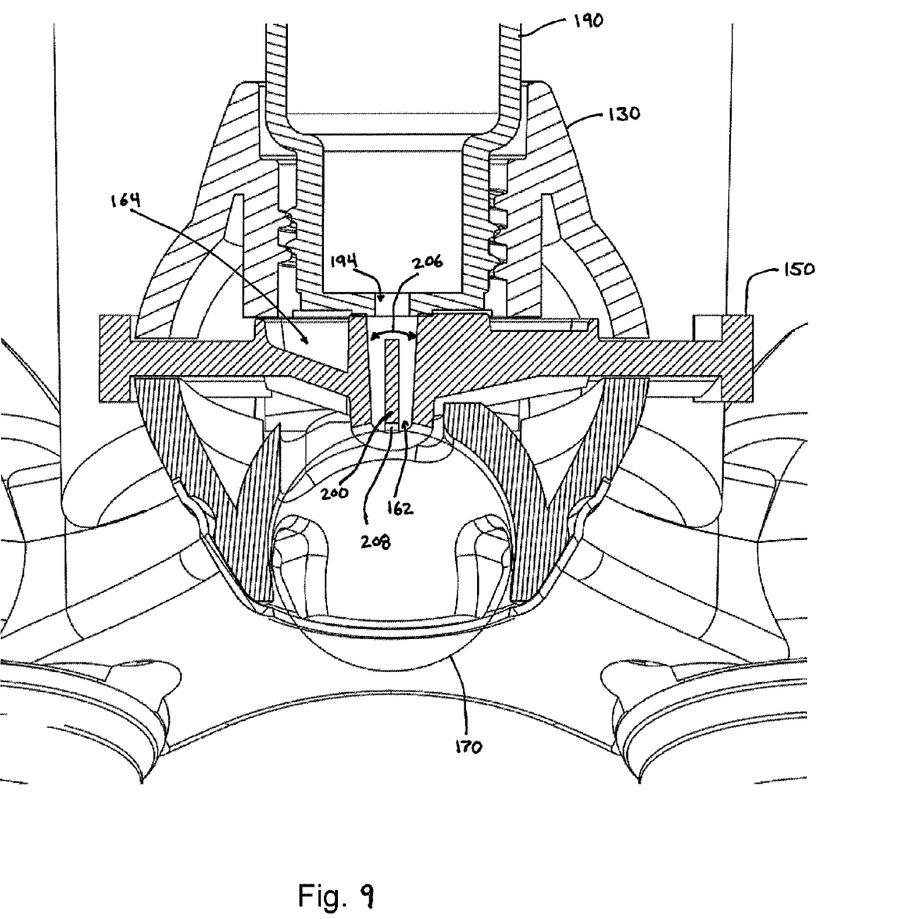
FIG. 9 is a cross-sectional view of a flow switch having a post with a channel when disposed within a roller ball foot, in accordance with some embodiments of the invention.

FIG. 9 depicts an embodiment of flow switch 150 having post 200 with channel 162 when disposed within the roller ball foot 130. As shown, post 200 can be sized to extend less than the entire length of channel 162 and/or so that it does not extend out of channel 162 toward the flow insert 192 of bottle 190. Moreover, a first end 208 of post 200 can be connected to the inner surface of the channel 160 on the end of channel 162 closest to the roller ball 170. As such, in operation, the non-connected, second end 210 of post 200 can vibrate in a side-to-side direction 206. When the vibrating second end 210 of post 200 contacts oil within channel 200, the vibration may induce the oil to flow through channel 200 and out onto roller ball 170.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, examples are meant to be illustrative only and should not be construed to be limiting in any manner.

We claim:

1. A device for applying topical oils to an individual, the device comprising:
   an applicator body containing a vibration assembly;
   a roller ball foot coupled to the applicator body, the roller ball foot housing a roller ball;
   a container detachably coupled to the roller ball foot, the container being configured to hold topical oil; and
   a flow switch disposed between the container and the roller ball, the flow switch comprising a channel and a post, wherein a continuous channel wall extending between the container and the roller ball defines the channel and the post is entirely disposed within the channel, wherein the post comprises a first end coupled to the continuous channel wall and a second end that is free standing, the flow switch being configured to selectively control flow of topical oil from the container to the roller ball.

2. The device of claim 1, wherein the flow switch further comprises a post support wherein the first end of the post is coupled to the continuous channel wall via the post support and the second end is configured to vibrate in a side-to-side direction within the channel.

3. The device of claim 2, wherein the channel is shaped and sized such that surface tension of the topical oil to limits fluid flow through the channel absent vibration of the post during activation of the vibration assembly.

4. The device of claim 3, wherein the channel is shaped and sized such that when the post vibrates in response to vibration of the vibration assembly, the surface tension of the topical oil is changed to permit fluid flow through the channel.

5. The device of claim 1, wherein the flow switch is selectively movable between a first position and a second position with respect to the container, in the first position a stopper of the flow switch is positioned adjacent an opening in the container, and in the second position a channel of the flow switch is positioned adjacent to the opening in the container.

6. The device of claim 1, wherein the at least one roller ball foot includes a retaining ring formed from metal.

7. The device of claim 6, wherein the metal of the retaining ring comprises aluminum.

8. The device of claim 1, further comprising two or more roller ball feet.

9. The device of claim 1, wherein the roller ball is formed from metal.

10. A device for applying topical oils to an individual, the device comprising:
    an applicator body containing a vibration assembly;
    a roller ball foot coupled to the applicator body, the roller ball foot housing a roller ball;
    a container detachably coupled to the roller ball foot, the container being configured to hold topical oil;
    a channel formed between the container and the roller ball, wherein a continuous channel wall extending between the container and the roller ball defines the channel; and
    a post entirely disposed within the channel, wherein the post comprises a first end coupled to the continuous channel wall via a post support and a second end that is free standing, wherein the second end is configured to vibrate in a side-to-side direction within the channel when the vibrational assembly is activated, wherein vibration of the post changes the surface tension of the topical oil to allow flow of the topical oil through the channel.

11. The device of claim 10, wherein the channel is formed within a flow switch disposed between the container and the roller ball, the flow switch being configured to selectively control flow of topical oil from the container to the roller ball through the channel formed through the flow switch.

12. The device of claim 11, wherein the flow switch is selectively movable between a first position and a second position with respect to the container, in the first position a stopper of the flow switch is positioned adjacent an opening in the container, and in the second position the channel of the flow switch is positioned adjacent to the opening in the container.

13. The device of claim 10, wherein the first end of the post is coupled to a portion of the continuous channel wall nearest the roller ball.

14. The device of claim 10, wherein the channel is shaped and sized such that surface tension of the topical oil to limits fluid flow through the channel absent vibration of the post during activation of the vibration assembly.

15. The device of claim 14, wherein the channel is shaped and sized such that to when the post vibrates in response to vibration of the vibration assembly, the surface tension of the topical oil is changed to permit fluid flow through the channel.

16. The device of claim 10, wherein the at least one roller ball foot includes a retaining ring formed from metal.

17. The device of claim 16, wherein the roller ball is formed from metal.

18. A method of controlling the flow of topical oil in a massaging applicator, the method comprising:
    placing topical oil in a container;
    coupling the container to roller ball foot having a roller ball, wherein a channel is formed between the container and the roller ball, wherein a continuous channel wall extending between the container and the roller ball defines the channel, wherein a post is entirely disposed within the channel wherein the post comprises a first end coupled to the continuous channel wall via a post support and a second end that is free standing; and
    activating a vibration assembly to apply massaging vibrations to the roller ball, the massage vibrations causing the second end of the post to vibrate in a side-to-side direction within the channel.

* * * * *